United States Patent [19]

Aiello

[11] Patent Number: 6,114,395
[45] Date of Patent: Sep. 5, 2000

[54] METHOD OF TREATING ATHEROSCLEROSIS

[75] Inventor: Robert J. Aiello, Waterford, Conn.

[73] Assignee: Pfizer Inc., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/955,313

[22] Filed: Oct. 21, 1997

Related U.S. Application Data

[60] Provisional application No. 60/031,274, Nov. 15, 1996.

[51] Int. Cl.$^7$ .................................................. A61K 31/135
[52] U.S. Cl. ................................................ 514/648
[58] Field of Search ............................................. 514/648

[56] References Cited

U.S. PATENT DOCUMENTS

| | | | |
|---|---|---|---|
| 5,047,431 | 9/1991 | Schickaneder et al. | 514/648 |
| 5,254,594 | 10/1993 | Niikura et al. | 514/648 |
| 5,426,123 | 6/1995 | Fontana | 514/648 |

FOREIGN PATENT DOCUMENTS

| | | | |
|---|---|---|---|
| 4401554 A1 | 8/1994 | Germany | 514/648 |
| 4320898 | 1/1995 | Germany. | |
| WO9602242 | 2/1996 | WIPO. | |

OTHER PUBLICATIONS

Urabe, et al, Kyoto–furitsu Ika Daigaku Zasshi 104(12):1535–1544, 1995, "Atheroprotective affect of estrogen on human vascular cells".

Ross, Nature vol. 362, Apr. 29, 1993, pp. 801–808, "the pathogenesis of atherosclerosis: a perspective for the 1900s".

Maija Kaartinen, et al., Accumulation of Activated Mast Cells in the Shoulder Region of Human Coronary Atheroma, the Predilection Site of Atheromatous Rupture, vol. 90, No. 4, Circulation, pp. 1669–1678, Oct. 1994.

Valentin Fuster, Mechanism Leading to Myocardial Infarction: Insights from Studies of Vascular Biology, vol. 90, No. 4, Circulation, pp. 2126–2146, Oct. 1994.

Helen Wiseman, et al., Tamoxifen Inhibits Lipid peroxidaton in Cardiac Microsomes, vol. 45, No. 9, Biochemical Pharmacology, pp. 1851–1855, 1993.

C. J. Schwartz, et al., The Pathogenesis of Atherosclerosis: An Overview, vol. 14, Clin. Cardiol., pp. I–1–I–16, Feb. 1991.

M. R. Frazier' Jessen, et al., Estrogen Modulation of JE/Monocyte Chemoattractant Protein–1 mRNA Expression in Murine Macrophages, Journal of Immunology, vol. 154, No. 4, pp. 1838–1844, 1995.

David J. Grainer, et al., Tamoxifen Elevates Transforming Growth Factor–β and Supresses Diet–induced Formation of Lipid Lesions in Mouse Aorta, vol. 1, No. 10, Nature Medicine, pp. 1067–1073, Oct. 1995.

Helen Wiseman, et al., Droloxifene(3–hydroxytamoxifen) has Membrane Antioxidant Ability: Potential Relevance to its Mechanism of Therapeutic Action in Breast Cancer, 66, Cancer Letters, pp. 61–68, 1992.

*Primary Examiner*—Jerome D. Goldberg
*Attorney, Agent, or Firm*—Peter C. Richardson; Gregg C. Benson; Steven W. Collier

[57] ABSTRACT

A method of treating atherosclerosis, independent of lipid lowering, in mammals, including humans, in need of treatment by inhibiting progression of an atherogenic lesion or by stabilizing plaque. Such lesion progression inhibition or plaque stabilization is achieved by directly inhibiting chemokine expression leading to excessive inflammatory cell recruitment by administering a therapeutically effective amount of a compound of formula I.

12 Claims, No Drawings

METHOD OF TREATING ATHEROSCLEROSIS

This application claims the benefit of U.S. Provisional Application Ser. No. 60/031,274 filed Nov. 15, 1996.

BACKGROUND OF THE INVENTION

This invention relates to a method of treating atherosclerosis in mammals, including humans, with certain estrogen agonists/antagonists.

Myocardial infarction is the leading cause of death in western countries, accounting annually for more than 500,000 deaths in the United States alone. Coronary artery stenosis and the number of diseased vessels are accepted markers of cardiac morbidity and mortality. The rupture of unstable atherosclerotic plaques contributes to nearly 75% of all myocardial infarctions and strokes. However, angiography does not predict future sites of occlusion and or rupture. Recent studies suggest that 72% of coronary events are not of severe calcified, fibrotic lesions but rather from rupture of mildly stenotic lipid rich plaques, often not visible by angiography (*Circulation.* 1994: 90:4: 2126–2146). Several recent studies have shown that increased macrophage infiltration is associated with erosion of the extracellular matrix of an atherosclerotic lesion, weakening of the lesion cap and increased vulnerability to rupture (*Circulation.* 1994:90:1669–1678.). It has been suggested that uncontrolled monocyte infiltration leads to excessive lipid accumulation and increased extracellular breakdown of the fibrous cap of the atherosclerotic lesion, thus triggering thrombosis. It has also been suggested that an inhibitor of the pro-inflammatory responses, will enhance plaque stability by preventing excessive monocyte infiltration.

Also, Wiseman, et al. Biochem. Pharm. 45, No. 9, 1851 (1993) has described the role of lipid peroxidation in cardiovascular injury and the development of atherosclerosis. In addition, Wiseman et al. Cancer Letters 66, 61 (1992) has disclosed that droloxifene inhibits lipid peroxidation. Also, U.S. Pat. No. 5,047,431 discloses the use of droloxifene for the treatment of hormone dependent mammary tumors and U.S. Pat. No. 5,254,594 discloses the use of droloxifene for the relief of bone diseases caused by the deficiency of estrogen. U.S. Pat. No. 5,426,123 discloses the lipid lowering effects of droloxifene.

In addition Grainger, et al., Nature Medicine, Vol. 1, No. 10 (October 1995) have disclosed Tamoxifen suppresses diet-induced formation of lipid lesions in mouse aorta.

Thus, although there exist a variety of anti-atherosclerotic therapies there is a continuing need and a continuing search in this field of art for alternative therapies for treating atherosclerosis.

SUMMARY OF THE INVENTION

This invention is directed to a method of treating atherosclerosis, independent of lipid lowering in mammals, including humans, in need of treatment by inhibiting progression of an atherogenic lesion or by stabilizing plaque. Such lesion progression inhibition or plaque stabilization is achieved by directly inhibiting chemokine expression leading to excessive inflammatory cell recruitment by administering a therapeutically effective amount of a compound of formula I.

The above described effects (inhibiting atherogenic progression and stabilizing plaque) occur through inhibition of the recruitment of inflammatory cells by directly controlling the expression of a gene. This direct control of the expression of a gene is distinct from the inhibition of the peroxidation of lipids because it involves the direct controlling of chemokines at the DNA level rather than indirectly preventing gene expression by preventing lipid oxidation through the known antioxidant properties of estrogen like compounds. This is independent of the known lipid lowering effects of these compounds.

The compounds of formula I have the formula

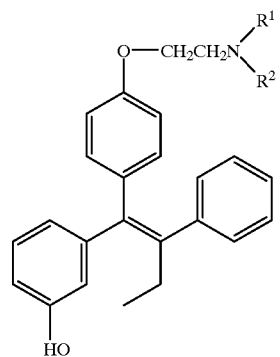

(I)

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof. A preferred compound of formula I is that in which $R^1$ and $R^2$ are methyl. A preferred salt is the citrate salt.

A preferred dosage for the above methods is about 0.01 to 200 mg/kg/day, preferably 0.5 to 100 mg/kg/day.

By lesion progression is meant increased monocyte recruitment, growth with smooth muscle cell proliferation, migration, and matrix synthesis, and degeneration with cellular and extra cellular lipid accumulation.

By plaque stabilization is meant the inhibition of plaque passing through a phase in which the lipid core has grown and the fibrous cap is very thin and vulnerable to rupture due to an increase density of macrophages.

By chemokines is meant specific chemoattractant cytokine for monocytes belonging to the C—C (β) subfamily of chemokines including MIP-1a, MIP-1β, RANTES, MCP-1, MCP-2 and MCP-3 which are produced by endothelial cells, smooth muscle cells and macrophages found in the vessel wall.

By direct inhibition of chemokine expression is meant the inhibition of gene expression by interaction with a transcriptional element or factor that binds directly to the DNA, thus preventing the expression of that gene. Control of transcription is exercised at the level of initiation of mRNA synthesis.

By excessive monocyte recruitment is meant an inflammatory response leading to the accumulation of macrophages in the arterial wall due to the transendothelial migration of monocytes into the intimal space.

The term "treating", "treat" or "treatment" as used herein includes preventative (e.g., prophylactic) and palliative treatment.

Other features and advantages will be apparent from the specification and claims which describe the invention.

DETAILED DESCRIPTION OF THE INVENTION

The compounds of this invention inhibit the formation (e.g., progression) of atherosclerotic plaques and also aid in stabilizing plaques. In general, it is believed that several potential molecular targets may mediate this effect including pro inflammatory chemokines (e.g., MCP-1). MCP-1 is a potent chemoattractant factor for monocytes and macrophages. It is produced and secreted by endothelial cells, vascular smooth muscle cells and macrophages in response to inflammatory mediators such as IL-1 and oxidized lipids.

More particularly, it is believed that modification of low-density lipoprotein (LDL) by reactive oxygen species into oxidatively modified LDL (Ox-LDL) is central to the initiation of atherosclerosis. Areas of the vessel wall prone to plaque formation accumulate circulating LDL. Endothelial, smooth muscle and/or inflammatory cells then convert the LDL to Ox-LDL. Consequently, monocyte become engorged with Ox-LDL forming macrophage foam cells. The Ox-LDL and other risk factors activate genes within macrophages and other inflammatory cells to promote additional recruitment of inflammatory cells to the artery or vein vessel wall. The compounds of this invention are believed to limit the recruitment of inflammatory cells into the vessel wall which lead to atherosclerotic plaque progression by controlling the transcription of genes, such as Monocyte Chemoattractant Protein-I (MCP-1), involved with the chemotaxis of monocytes at the level of mRNA synthesis. For example, as a result of our analysis of the lipid-fed ApoE KO mouse it is believed that the compounds of this invention lower the high levels of MCP-1 mRNA seen in the atherosclerotic lesions. The reduced levels of MCP-1 mRNA result in significant changes in monocyte migration resulting in the inhibition of atherogenic lesion progression.

The compounds of this invention also aid in stabilizing plaques. It is believed that early in the development of atherosclerotic plaques, all plaques pass through a phase in which the lipid core has grown and the fibrous cap is very thin and vulnerable to rupture. There is a great deal of evidence implicating macrophages (which secrete proteases and lipases) in the degradation of the fibrous cap. Davies et al (Br. Heart J. 1985; 53: 363–373) have described increased density of macrophages in ruptured plaques in comparison with stable plaques. Moreover the immediate site of plaque rupture or erosion is always marked by an inflammation process. The compounds of this invention also stabilize plaque by inhibiting monocyte (e.g., inflammatory cell) recruitment (e.g., monocyte infiltration) into the arterial wall leading to breakdown of the fibrous cap of the atherosclerotic lesion. This inhibition of monocyte recruitment occurs by directly inhibiting the expression of chemokines such as MCP-1 that results in excessive monocyte infiltration and foam cell formation in the arterial wall.

The above described effects (1. inhibiting atherogenic progression and 2. stabilizing plaque) occur through inhibiting the recruitment of inflammatory cells by directly controlling the expression of a gene. This direct controlling the expression of a gene is distinct from the inhibition of the peroxidation of lipids because it involves the direct controlling of chemokines at the DNA level rather than indirectly preventing gene expression by preventing lipid oxidation through the known antioxidant properties of estrogen like compounds.

The methods of this invention are practiced by administering to an individual in need of treatment an effective amount of a compound formula I

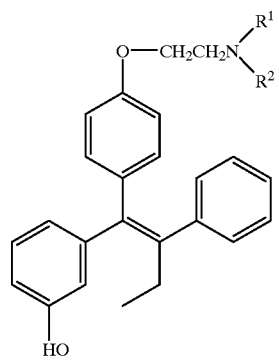

(I)

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group; or a pharmaceutically acceptable salt thereof.

Compounds of formula I are known in the art and essentially are prepared via the methods described in U.S. Pat. No. 5,047,431, the disclosure of which is hereby incorporated herein by reference.

A preferred formula I compound is that in which $R^1$ and $R^2$ each are methyl. This preferred compound is known as droloxifene, (E)-1-[4'-(2-Dimethylaminoethoxy)phenyl]-1-(3-hydroxyphenyl)-2-phenylbut-1-ene, which previously has been described as an antiestrogenic agent and is useful for the treatment of hormone dependent mammary tumors (U.S. Pat. No. 5,047,431), and for the relief of bone diseases caused by the deficiency of estrogen or the like (U.S. Pat. No. 5,254,594).

Although the free-base form of formula I compounds can be used in the methods of the present invention, it is preferred to prepare and use a pharmaceutically acceptable salt form. Thus, the compounds used in the methods of this invention form pharmaceutically acceptable acid and base addition salts with a wide variety of inorganic and, preferably, organic acids and include the physiologically acceptable salts which are often used in pharmaceutical chemistry. Such salts are also part of this invention. Typical bases include sodium hydroxide and potassium hydroxide. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the citrate salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means. In an analogous manner the pharmaceutically base addition salts may be prepared.

The pharmaceutically acceptable salts of formula I compounds generally have enhanced solubility characteristics compared to the compound from which they are derived, and thus are often more amenable to formulation as liquids or emulsions.

Once prepared, the free base or salt form of formula I compounds can be administered to an individual in need of treatment for the methods herein described.

Some of the compounds of this invention have asymmetric carbon atoms and therefore are enantiomers or diastereomers. Diastereomeric mixtures can be separated into their individual diastereomers on the basis of their physical chemical differences by methods known per se., for example, by chromatography and/or fractional crystallization. Enantiomers can be separated by converting the enantiomeric mixture into a diastereomeric mixture by reaction with an appropriate optically active compound, separating the diastereomers and converting (e.g., hydrolyzing) the individual diastereomers to the corresponding pure enantiomers. All such isomers, including diastereomers, enantiomers and mixtures thereof are considered as part of this invention.

The methods of this invention are all adapted to therapeutic use by either inhibiting the recruitment of inflammatory cells by controlling gene expression or stabilizing plaque in mammals, particularly humans. Since these functions are closely related to the development of atherosclerosis and coronary heart disease related disorders, these methods prevent, arrest, regress or reverse atherosclerosis.

The utility of the compounds of the present invention as medical agents in the treatment of atherosclerosis in mammals (e.g., humans, particularly the female) is demonstrated by the activity of the compounds of this invention in conventional assays and the in vivo assays described below. Such assays also provide a means whereby the activities of the compounds of this invention can be compared between themselves and with the activities of other known compounds. The results of these comparisons are useful for determining dosage levels in mammals, including humans, for the treatment of such diseases.

The anti-atherosclerotic activity of these compounds can be determined by assessing the effect of these compounds, compared to placebo control, (administered subcutaneously, in ovariectomized female Apo E deficient mice fed a high fat diet) on the percent of the aortic surface covered by atherosclerotic lesions.

PROTOCOL

Animal Prep: Ovariectomized female, Apo E deficient mice are placed on a high fat diet. The animals are divided into control groups and test compound groups. The compound to be tested and placebo (contained in 60-day release subdermal pellets) are inserted beneath the skin at the back of the animal's neck with a trochar. The animals are redosed approximately 55 days after the initial dosing to allow the mice a total dosing period of approximately 90 days.

ANIMALS

Female, Apo E deficient transgenic mice
20 to 30 gram average weights
OVX at 25 days of age
Placed in individual isolation cages upon start of study
Dosed at 70 days of age for 90 days
Fed a Western-type diet containing 21% fat and 0.15% cholesterol (% by weight)
(Harlan Teklad, Madison, Wis., Cat.# TD 88137 TEKLAD) for 3 months prior to sacrifice.
Sacrificed at 155 days of age

TIME RELEASE PELLETS

Time release pellets (60-day, 30 mm) were obtained from Innovative Research of America (1-800-421-8171) as follows:

Placebo: 5 mg pellet (83 ug/day) CAT #SC-111 obtained from Innovative Research of America (1-800421-8171)

Test compound: pellet CAT # special order obtained from Innovative Research of America (1-800421-8171)

Tissue Collection: At the end of the 90 day dosing period, the animals are fasted overnight prior to sacrifice. The animals are anesthetized and a whole blood sample is removed from each animal for analysis of plasma cholesterol and triglycerides. The mice are perfused in situ with PBS (via heart puncture in the left ventricle) for a short period or until the tissues are free of blood (perfusate is clear). The perfusate is switched to 4% cacodylate-buffered paraformaldehyde and the animal is perfusion fixed in situ for a short period. The uterus is removed and weighed. The heart and aorta (from the arch at the heart to just below the renal branch) are removed and transferred to separate vials containing 4% cacodylate- buffered paraformaldehyde. The tissues are post perfusion fixed for a few hours. The tissues are transferred to 30% gum sucrose and the sucrose is allowed to infiltrate the tissues for at least a day prior to sectioning.

Aorta: The exterior adventitia is removed from the aorta and the vessel is cut open by making a longitudinal cut along the side of the aorta starting at the arch and working down to the femoral branch. A second longitudinal cut is made on the other side of the aortic arch to split the vessel in half at this point. The amount of lesion is quantitated in the aortic vessel using for example, an OPTIMAS image analysis program ('OPTIMAS 4.1 software (Image Processing Solutions, Woburn, Mass.)). The aortas are stored in 10% buffered formalin.

Heart: The hearts are imbedded in OCT and cryostat sections of the aortic sinus and the aortic valve of the heart are made. 10 µm sections are taken and every other section is saved on Vectabond coated slides. Each region of the aorta should encompass approx. 3–4 slides w/4 sections per slide. The heart sections are stained for lipid with Oil Red O and the amount of lesion is quantitated in the aortic sinus and/or the aortic valve area using the OPTIMAS image analysis program.

Administration of the compounds of this invention can be via any method which delivers a compound of this invention systemically. These methods include oral routes, parenteral, intraduodenal routes, etc. Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug. The compounds of this invention can be singly or co-administered simultaneously or sequentially in any order.

In any event the amount and timing of compound(s) administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the activity (i.e., antiatherosclerotic effect) that the physician considers appropriate for the individual patient. In considering the degree of activity desired, the physician must balance a variety of factors such as atherosclerotic starting level, age of the patient, as well as presence of other diseases (e.g., osteoporosis). For example, the administration of an estrogen agonist/antagonist can provide osteoporosis benefits particularly, for post-menopausal women. The following paragraphs provide preferred dosage ranges or the various compounds of this invention.

The amount of the compound of this invention to be used is determined by its activity as an antiatherosclerotic agent. This activity is determined by means of an individual compound's pharmacokinetics and its minimum maximal effective dose in inhibition of plaque formation and/or stabilization using a protocol as described above.

In general an effective dosage for the antiatherosclerotic activities of this invention, for the compounds of this invention, is in the range of 0.01 to 200 mg/kg/day, preferably 0.10 to 100 mg/kg/day.

The compounds of the present invention are generally administered in the form of a pharmaceutical composition comprising at least one of the compounds of this invention together with a pharmaceutically acceptable vehicle or diluent. Thus, the compounds of this invention can be administered individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easter, Pa., 15th Edition (1975).

Pharmaceutical compositions according to the invention may contain 0.1%–95% of the compound(s) of this invention, preferably 1%–70%. In any event, the composition or formulation to be administered will contain a quantity of a compound(s) according to the invention in an amount effective to treat the disease/condition of the subject being treated.

EXAMPLE 1

This EXAMPLE compares the amount of atherosclerotic lesion found in ovariectomized female Apo E deficient mice fed a high fat diet and dosed subcutaneously with placebo, 17-beta estradiol, or {4-[2-(2-aza-bicyclo[2.2.1]hept-2-yl)-ethoxy]-phenyl}-[6-hydroxy-2-(4-hydroxy-phenyl)-benzo[b]thiophen-3-yl]-methanone, for 90 days. The latter compound, and methods of making it, are disclosed in publication no. WO 95/10513.

Animals

Homozygous apolipoprotein (apo)E-deficient mice were bred in house. The mice had a mixed genetic background (129olax×C57B/6). Thirty-six mice were maintained in a 12 hour light/dark cycle room with free access to food and water. The mice were fed an adjusted calories "Western-type" diet (Harlan Teklad, Madison, Wis., Cat.# TD 88137, containing 21% fat and 0.15% cholesterol by weight). At weaning (age 28 days), female mice were bilaterally ovariectomized (OVX) or sham operated through a one centimeter dorsal incision. At 45 days of age, the mice were randomly assigned to one of three treatment groups and 60-day slow-release pellets (Innovative Research of America, Toledo, Ohio) were inserted interscapularly under anesthesia: 0.5 mg placebo, 6 µg per day of 17-beta estradiol, or 50 µg per day of {4-[2-(2-aza-bicyclo[2.2.1] hept-2-yl)-ethoxy]-phenyl}-[6-hydroxy-2-(4-hydroxy-phenyl)-benzo[b]thiophen-3-yl]-methanone. The mice were redosed after 55 days to allow for a total dosing period of 90 days.

Tissue Preparation

After an overnight fast, the mice were anesthetized with Ketamine/Xylazine/PLBS 1:1:2 (Miles Inc). Blood and uteri were then removed followed by in situ perfusion (80 mm$^2$ hg) with phosphate buffered saline (PBS) pH 7.4.

Sections were prepared for lipid staining and morphometric analysis as follows. Hearts were perfusion fixed in situ with 4% cacodylate-buffered paraformaldehyde. The heart and aorta were removed and fixed for an additional 2 to 3 hours in 4% cacodylate-buffered paraformaldehyde followed by infiltration with 30% gum sucrose (1% gum arabic+30% sucrose in PBS) for 24 hours, 4° C. To determine cross-sectional lesion area, hearts were embedded in OCT imbedding medium (Optimal Cryostat Temperature Inc.) and cryostat sectioned at 10μ, −18° C. Every other section was mounted on Vectabond (Vector Laboratories, Inc., Burlingame, Calif.) coated slides. The area of the heart to be sectioned was divided into two separate regions commonly used for quantitating the degree of atherosclerotic lesions in mice, the aortic sinus and the aortic valve. When moving up from the base of the heart, the sinus began at the first appearance of the valve cusps dividing the lumen into three distinct regions. In this region, the aortic wall is bulging and irregular. The sinus region ends and the valve region begins when the valve cusps no longer divide the lumen and the wall appears more rounded and distinct. The valve began at the end of the sinus and continued until the valve cusps were no longer apparent and the wall was well rounded (approximately 280 μm). Sections were stained for lipid with Oil red O (0.5% in propylene glycol, Polyscientific, BayShore, N.Y.) and counterstained with Gill's III Hematoxylin (Sigma).

Lesion Analysis

Each section of the aortic sinus and the aortic valve was evaluated for Oil red O staining area by capturing images directly from a camera attached to a Leitz Laborlux S (Leica) light microscope and displaying them on a Trinitron RGB monitor. Image analysis was determined using 'OPTIMAS 4.1 software (Image Processing Solutions, Woburn, Mass.). The outer and inner perimeters of the aortic wall in cross sections were delineated and thresholds were set to distinguish between normal (hematoxylin stained) and diseased (Oil red O stained) tissue. The results were expressed as the average lesion size per section or as the percent of the total cross sectional vessel wall area (normal+diseased area/section, excluding the lumen) stained with Oil red O. For each animal, the average of 12 to 6 sections was determined and data are expressed as lesion size or mean percent lesion area.

The percent of the aortic surface covered by lesions was determined using an en face preparation. Aortas infiltrated with gum sucrose as described above were cleaned of adventitia and a longitudinal cut was made from the arch down toward the femoral branch. A second longitudinal cut was made between the coronary and carotid arteries in the aortic arch and the aorta was laid open on a piece of polystyrene. Each aorta was evaluated for lesion area by direct image capture from a CCD camera attached to a copy stand and displayed on a Trinitron monitor. The lesion area was determined in unstained tissue using 'OPTIMAS 4.1 image analysis. Areas of atherosclerotic plaques in aortas cleaned of adventita appear as yellowish-white areas. This area was quantitated by manually setting thresholds for shades of black (background), gray (normal tissue) and white (lesion area).

Plasma lipids

Total plasma cholesterol and triglycerides were measured using colorimetric methods with commercially available kits (Wako and Boehrringer-Mannheim).

Statistical Analysis

Analysis of variance (ANOVA) was used to test for statistically significant differences between the groups with regard, treatment, serum lipids and lesion size. Fisher's F test was used to determine significant differences among means.

Results

The results of the Example are detailed in the following Table. The data demonstrates the validity of the protocol by demonstrating the reduction in atherosclerotic lesion size for the estrogen agonist {4-[2-(2-aza-bicyclo[2.2.1]hept- 2-yl)-ethoxy]-phenyl}-[6-hydroxy-2-(4-hydroxy-phenyl)-benzo[b]thiophen-3-yl]-methanone. Importantly, this occurred without a reduction in cholesterol as the cholesterol lowering activity of the estrogen agonist was not observed in this experiment, either because the compound was administered subcutaneously rather than orally or mice are non-responsive to estrogen-like compounds with regard to lipid effects.

TABLE

{4-[2-(2-Aza-bicyclo[2.2.1]hept-2-yl)-ethoxy]-phenyl}-
[6-hydroxy-2-(4-hydroxyphenyl)-benzo[b]thiophen-3-yl]-
methanone Reduces Lesion Size in OVX apoE-Deficient
Mice Without Affecting Plasma Lipids or Uterine Weight

| Group | N | Total Cholesterol (mg/dl) | Tri-glycerides (mg/dl) | Uterine WT (gm) | Aortic Valve Lesion area (%) |
|---|---|---|---|---|---|
| Placebo | 15 | 929 ± 315 | 96 ± 24 | 37 ± 39 | 33.4 ± 11.2 |
| 17-beta estradiol (6 μg/d) | 8 | 641 ± 172* | 53 ± 24* | 165 ± 105* | 18.9 ± 6.2* |
| X(50 μg/d) | 10 | 820 ± 134 | 91 ± 55 | 35 ± 15 | 21.2 ± 6* |

*Significant difference from placebo (P is less than 0.05)
X is {4-[2-(2-aza-bicyclo[2.2.1]hept-2-yl)-ethoxy]-phenyl}-[6-hydroxy-2-(4-hydroxyphenyl)-benzo[b]thiophen-3-yl]-methanone It should be understood that the invention is not limited to the particular embodiments described herein, but that various changes and modifications may be made without departing from the spirit and scope of this novel concept as defined by the following claims.

I claim:

1. A method of inhibiting chemokine expression in a mammal in need thereof, comprising administering to said mammal, an effective amount of a compound of formula I

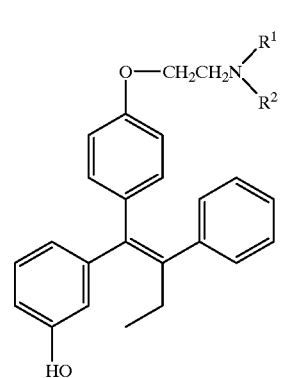

(I)

wherein
$R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group;

or a pharmaceutically acceptable salt thereof.

2. A method according to claim 1 wherein the compound of formula I is a compound wherein $R^1$ and $R^2$ each are methyl, or a pharmaceutically acceptable salt thereof.

3. A method according to claim 2 wherein said salt thereof is the citrate salt.

4. A method as recited in claim 3 wherein the mammal is a human.

5. A method as recited in claim 4 wherein the amount is from about 0.01 mg/kg/day to about 200 mg/kg/day.

6. A method as recited in claim 5 wherein the amount is from about 0.10 mg/kg/day to about 100 mg/kg/day.

7. A method of inhibiting an inflammation process in a mammal in need thereof comprising administering to said mammal, an effective amount of a compound of formula I

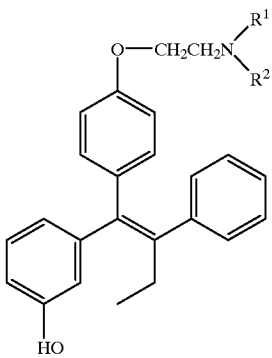

(I)

wherein $R^1$ and $R^2$ may be the same or different provided that, when $R^1$ and $R^2$ are the same, each is a methyl or ethyl group, and, when $R^1$ and $R^2$ are different, one of them is a methyl or ethyl group and the other is hydrogen or a benzyl group;

or a pharmaceutically acceptable salt thereof.

8. A method according to claim 7 wherein the compound of formula I is a compound wherein $R^1$ and $R^2$ each are methyl, or a pharmaceutically acceptable salt thereof.

9. A method according to claim 7 wherein said salt thereof is the citrate salt.

10. A method as recited in claim 9 wherein the mammal is a human.

11. A method as recited in claim 10 wherein the amount is from about 0.01 mg/kg/day to about 200 mg/kg/day.

12. A method as recited in claim 11 wherein the amount is from about 0.10 mg/kg/day to about 100 mg/kg/day.

* * * * *